United States Patent
Krauss

(10) Patent No.: US 7,940,893 B2
(45) Date of Patent: May 10, 2011

(54) METHOD FOR DISTINGUISHING BETWEEN FOUR MATERIALS IN TOMOGRAPHIC RECORDS OF A DUAL-ENERGY CT SYSTEM

(75) Inventor: Bernhard Krauss, Bugthann (DE)

(73) Assignee: Siemens Aktiengesellschaft, Munich (DE)

( * ) Notice: Subject to any disclaimer, the term of this patent is extended or adjusted under 35 U.S.C. 154(b) by 461 days.

(21) Appl. No.: 12/081,159

(22) Filed: Apr. 11, 2008

(65) Prior Publication Data
US 2008/0253508 A1  Oct. 16, 2008

(30) Foreign Application Priority Data

Apr. 12, 2007 (DE) .................... 10 2007 017 629

(51) Int. Cl.
*G01N 23/087* (2006.01)
(52) U.S. Cl. ................ 378/98.9; 378/5; 378/53
(58) Field of Classification Search .................. 378/4, 5, 378/9, 16, 53, 57, 98.9, 98.11
See application file for complete search history.

(56) References Cited

U.S. PATENT DOCUMENTS

| | | | |
|---|---|---|---|
| 5,668,374 A * | 9/1997 | DiFoggio et al. | 250/339.12 |
| 6,987,833 B2 | 1/2006 | Du et al. | |
| 2004/0101088 A1 | 5/2004 | Sabol et al. | |
| 2004/0184574 A1 | 9/2004 | Wu et al. | |
| 2006/0251209 A1 | 11/2006 | Tkaczyk et al. | |
| 2007/0030944 A1 | 2/2007 | Grasruck et al. | |
| 2007/0092127 A1* | 4/2007 | Grasruck et al. | 382/132 |
| 2008/0013672 A1 | 1/2008 | Krauss et al. | |
| 2008/0037699 A1 | 2/2008 | Krauss | |

FOREIGN PATENT DOCUMENTS

| | | |
|---|---|---|
| DE | 10 2005 049 602 B3 | 4/2007 |
| DE | 102005037367 | 4/2007 |
| DE | 102006015451 | 10/2007 |
| DE | 102006015452 | 10/2007 |

\* cited by examiner

*Primary Examiner* — Edward J Glick
*Assistant Examiner* — John M Corbett
(74) *Attorney, Agent, or Firm* — Harness, Dickey & Pierce, P.L.C.

(57) ABSTRACT

A method and a CT system are disclosed having a computation unit for distinguishing between four materials ($M_1$, $M_2$, $M_3$, $M_4$) in tomographic records of a dual-energy CT system, wherein the size of a two-dimensional or three-dimensional viewing area is defined around each voxel whose material content is to be distinguished. In an embodiment of the method, the adjacent voxels from the viewing area on an HU value diagram are imaged for each voxel ($V_i$) whose material content is to be distinguished, the distances from the diagonals are calculated for all the imaged voxels, and the mean squares of these distances are formed ($\langle x_1^2 \rangle$, $\langle x_2^2 \rangle$). If the mean square distance ($\langle x_1^2 \rangle$, $\langle x_2^2 \rangle$) to one diagonal is less than to the other diagonal, then the composition of the voxel is assumed to be composed of the materials to whose diagonal the lower mean square distance ($\langle x_1^2 \rangle$, $\langle x_2^2 \rangle$) occurs.

21 Claims, 3 Drawing Sheets

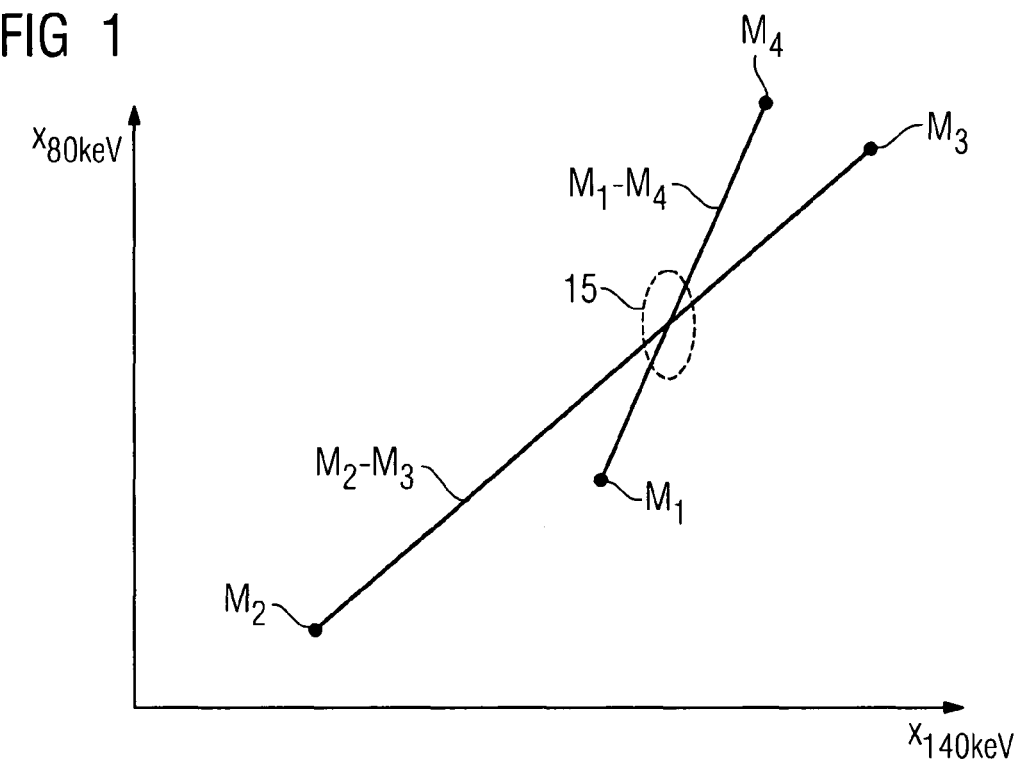
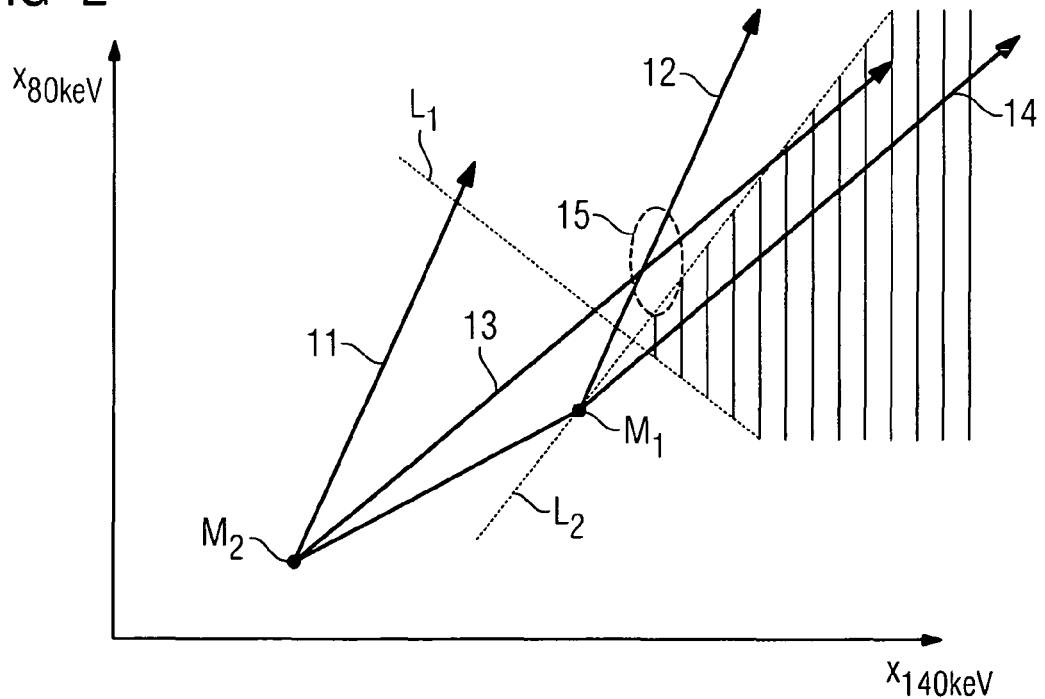

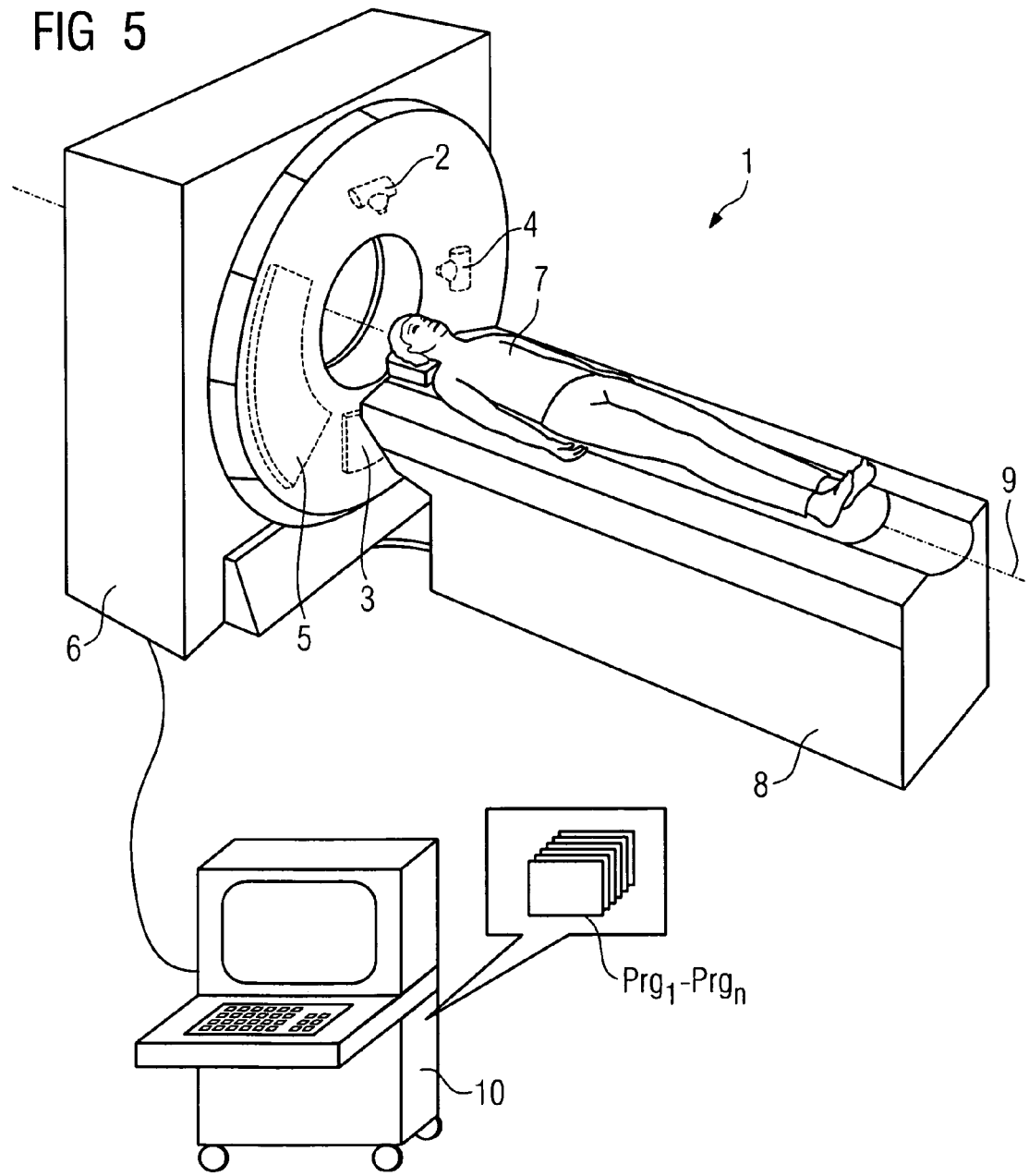

METHOD FOR DISTINGUISHING BETWEEN FOUR MATERIALS IN TOMOGRAPHIC RECORDS OF A DUAL-ENERGY CT SYSTEM

PRIORITY STATEMENT

The present application hereby claims priority under 35 U.S.C. §119 on German patent application number DE 10 2007 017 629.7 filed Apr. 12, 2007, the entire contents of which is hereby incorporated herein by reference.

FIELD

Embodiments of the invention generally relate to a method for distinguishing between four materials in tomographic records of a dual-energy CT system by scanning an examination area of an examination object, preferably of human or animal patient, containing at least four different materials, wherein the scanning is carried out using two different X-ray energy spectra from a multiplicity of projection directions, and absorption data is measured for each X-ray spectrum that is used, the HU values of four materials form a quadrilateral of an HU-value diagram of the X-ray energies used for scanning, the two diagonals of which quadrilateral intersect one another, the materials which form one diagonal are each mixed in the present case, and two materials which define a diagonal form a mixture with particle sizes in the same order of magnitude as the resolution of the CT system, and, furthermore, reconstruction of at least one first tomographic image data record from the absorption data of the first X-ray spectrum, and reconstruction of at least one second tomographic image data record from the absorption data of the second X-ray spectrum are carried out.

BACKGROUND

Methods for distinguishing between a plurality of materials using CT image or volume data which has been determined using two different X-ray spectra are generally known. However, in some cases, it is difficult to distinguish between specific materials in combinations of other materials using known dual-energy CT methods. For example, this is true of yellow bone marrow (that is to say fat) in the spongiosa with respect to a mixture of iodine in the blood or soft tissue. This distinction is not always possible, even without any image noise, for individual voxels as well as voxel regions over which the absorption is averaged.

SUMMARY

In at least one embodiment of the invention, a method is described which makes it possible to distinguish better between materials and material combinations.

The inventor has found, in at least one embodiment, that it is possible to obtain additional knowledge about the expected HU values of individual pixels/voxels of a possible composition of an examination object in the distinguishing process. The knowledge of specific mixing options or the knowledge of prevailing structures in the examination object can therefore be included in statistical and spatial examinations thus assisting decisions relating to the present material not only based on pure knowledge of measured HU values but also on possible distributions in three dimensions and possible mixtures of the materials being looked for. The position and distribution of HU value pairs on an HU value diagram, and statistical characteristic values calculated from them, can be used for this purpose.

In at least one embodiment, the inventor accordingly proposes that a known method for distinguishing between four materials in tomographic records of a dual-energy CT system be improved, with this method including:

Scanning of an examination area of an examination object, preferably of a patient, including at least four different materials, wherein:
  the scanning is carried out using two different X-ray energy spectra from a multiplicity of projection directions, and absorption data is measured for each X-ray spectrum that is used,
  the HU values of four materials form a quadrilateral on an HU-value diagram of the X-ray spectra used for scanning, the two diagonals of which quadrilateral intersect one another,
  the materials which form one diagonal are each mixed in the present case, and
  two materials which define a diagonal form a mixture with particle sizes in the same order of magnitude as the resolution of the CT system,
  reconstruction of at least one first tomographic image data record from the absorption data of the first X-ray spectrum,
  reconstruction of at least one second tomographic image data record from the absorption data of the second X-ray spectrum.

The method improvement according to at least one embodiment of the invention may result from the fact that:
  the size of a two-dimensional or three-dimensional viewing area around each voxel whose material content is to be distinguished is defined, and the subsequent statistical calculations are carried out in this viewing area,
  the adjacent voxels from the viewing area on an HU value diagram are imaged for each voxel whose material content is to be distinguished,
  the distances from the diagonals are calculated for all the imaged voxels, and the mean squares of these distances are formed, and
  if the mean square distance to one diagonal is less than to the other diagonal, then the composition of the voxel is assumed to be composed of the materials to whose diagonal the lower mean square distance occurs.

In one advantageous embodiment, the inventor additionally proposes that the method described above be carried out only for those voxels whose adjacent voxels in the viewing area, at least in one of the image data records, overshoot or undershoot a predetermined HU threshold value for a predetermined proportion. This ensures that the subsequent evaluation has adequate statistical significance and extended structures are actually present which are typical of the occurrence of specific materials in the object being examined. One example of this is the distribution of bone marrow in a patient's body.

Furthermore, it may also be advantageous, in at least one embodiment, before carrying out the method as in the paragraph above, to smooth at least one of the image data records in at least one direction and to continue with the association process according to at least one embodiment of the invention for the voxel under consideration only when the HU value in the smoothed image overshoots a threshold at this point. Specifically, this test makes it possible to exclude fine vessels which would otherwise lead to further ambiguities. This is because, when the central voxels in a vessel that is filled with iodine are located precisely on the connecting line between fat and bone on the HU-value diagram, the mixing process resulting from partial volume effects with the surrounding tissue leads to voxels which are located exactly on the connecting line between yellow bone marrow and bone. This makes it impossible to distinguish yellow bone marrow in the spongiosa. The range of the image smoothing that has been mentioned should in this case be matched to the apparent patient diameter since, for example, typical structures in the area with a small diameter, for example on the foot, are also finer than in areas with a large diameter, for example in the knee or abdomen.

This smoothing as described above can be carried out one-dimensionally or two-dimensionally on a plane, preferably on the axial slice image plane. However, three-dimensional smoothing can also be carried out in space.

The inventor also proposes that, in at least one embodiment, the statistical analyses include only those voxels whose HU values overshoot a predetermined threshold value in at least one image data record. This avoids the statistics being dominated by mixtures with adjacent third materials, for example fat, as well as a blood/iodine mixture in a vessel. In addition, a specific threshold value can be used for each image data record.

Furthermore, it may be advantageous if the only voxels which are included in the statistical analyses are those whose HU value, weighted as a function of the noise, from the two image data records overshoots a predetermined threshold value.

The HU value, weighted as a function of the noise, of each voxel can be calculated using:

$$r = -\frac{q^2}{m_{co,min}} \text{ and } x_m = \frac{x_{E1} - r \cdot x_{E2}}{1 - r},$$

where q corresponds to the ratio $q_{E1}/q_{E2}$ between the noise $q_{E1}$ of the first image data record with the first X-ray energy to the noise $q_{E2}$ of the second image data record with the second X-ray energy, and $m_{co,min}$ corresponds to a value which is between the gradients of the diagonals on the HU value diagram of the four materials.

The method as described above, in at least one embodiment, can be used particularly advantageously if blood is used as the first material, fat as the second material, bone as the third material and a contrast agent, preferably a contrast agent containing iodine, as the fourth material. Alternatively, for example for compatibility reasons, to reduce the contrast agent dose or to achieve better spreading in the HU value diagram, it is also possible to use a contrast agent containing lanthanoid with a material combination which can otherwise be examined equally advantageously.

Instead of choosing fat as the second material, it is also possible to choose air when looking at bone tissue in the vicinity of air.

Particularly in the case of the material combinations mentioned above, the signed mean distances to the two diagonals and the variance of the distances to the diagonals between bone and contrast agent are calculated with respect to the HU value diagram in addition to the mean squares of the distances, wherein the introduction of the variance in the method described below leads to the material mixture comprising the first and fourth materials being output as the result even when a homogeneous mixture of the first and second materials is mixed inhomogeneously with the fourth material. One precondition for this is that the mixture composed of the first and second materials on the HU value diagram must be considerably closer to the first material than the fourth material. This condition is generally satisfied for the materials that have been mentioned. In the situation in which:

the signed mean distance to the first diagonal is positive between the first and the fourth material and the variance of this distance of the voxels which are located in the viewed area is greater than the mean square distance from the second diagonal between the second material and the third material, or the mean square distance from the first diagonal is greater than the mean square distance from the second diagonal between the second material and the third material, it is assumed that the voxel under consideration is composed of the second and third materials.

Particularly when the noise ratio between the two image data records assumes very extreme values, that is to say the differences in the image noise between the image data records recorded using different X-ray spectra are very large, it may be advantageous to replace the mean square distances using the following formulae:

$$\langle x_1^2 \rangle \to \frac{\langle x_1^2 \rangle}{a_1^2 q^2 + b_1^2},$$

$$\langle x_2^2 \rangle \to \frac{\langle x_2^2 \rangle}{a_2^2 q^2 + b_2^2}$$

where q corresponds to the ratio $q_{E1}/q_{E2}$ between the noise $q_{E1}$ of the first image data record $B_{E1}$ with the first X-ray energy $E_1$ to the noise $q_{E2}$ of the second image data record $B_{E2}$ with the second X-ray energy $E_2$, and the coefficients $a_1$, $a_2$, $b_1$ and $b_2$ are calculated as follows:

$$a_1 = \frac{1}{\sqrt{1 + m_{M2-M3}^2}},$$

$$a_2 = \frac{1}{\sqrt{1 + m_{M1-M4}^2}},$$

$$b_1 = -\frac{m_{M2-M3}}{\sqrt{1 + m_{M2-M3}^2}}$$

$$b_2 = -\frac{m_{M1-M4}}{\sqrt{1 + m_{M1-M4}^2}}.$$

It should be noted that the proposed method can in principle also be used to distinguish between more than two mixtures, each composed of two materials. For this purpose, it is possible to calculate not just two alternatives but various hypotheses. That hypothesis with the minimum value is finally chosen. In general, the method can be used whenever the aim is to distinguish between mixtures of two materials in each case and the mixtures are sufficiently inhomogeneous that adequately different mixture ratios can be assumed in the vicinity of a voxel to be classified.

In the method according to at least one embodiment of the invention mentioned above, it is particularly advantageous for the algorithm to be highly tolerant to noise and for the segmentation areas not to be defined in the two-dimensional feature space. Furthermore, there is no need to carry out absolute segmentation and, instead, just two possible hypotheses are compared with one another. This avoids the need to search for suitable threshold values.

BRIEF DESCRIPTION OF THE DRAWINGS

The invention will be explained in more detail in the following text with reference to one example exemplary embodiment and with the aid of the figures, which illustrate only those features which are necessary for understanding of the invention.

The following reference symbols are used in this case: 1: dual-energy CT system; 2: first X-ray tube; 3: first detector system; 4: second X-ray tube; 5: second detector systems; 6: gantry housing; 7: patient; 9: system axis; 10: control and computation unit; 11: voxels which contain $M_2$ (fat) and $M_4$ (iodine); 12: voxels which contain $M_1$ (blood) and $M_4$ (iodine); 13: voxels which contain $M_2$ (fat) and $M_3$ (bone); 14: voxels which contain $M_1$ (blood) and $M_3$ (iodine); 15: region of non-unique HU value association; 16: typical distribution of voxel in a region which contains bone and yellow bone marrow; $B_{E1}$: first image data record; $B_{E2}$: second image data record; $E_1$: first energy spectrum; $E_2$: second energy spectrum; $L_1$, $L_2$: separating lines; $Prg_1$-$Prg_n$: computer programs, $x_{80keV}$: HU values from a scan with X-ray radiation of the maximum energy 80 keV, $x_{140keV}$: HU values from a scan with X-ray radiation of maximum energy 140 keV.

In the figures, in detail:

Figure 3:
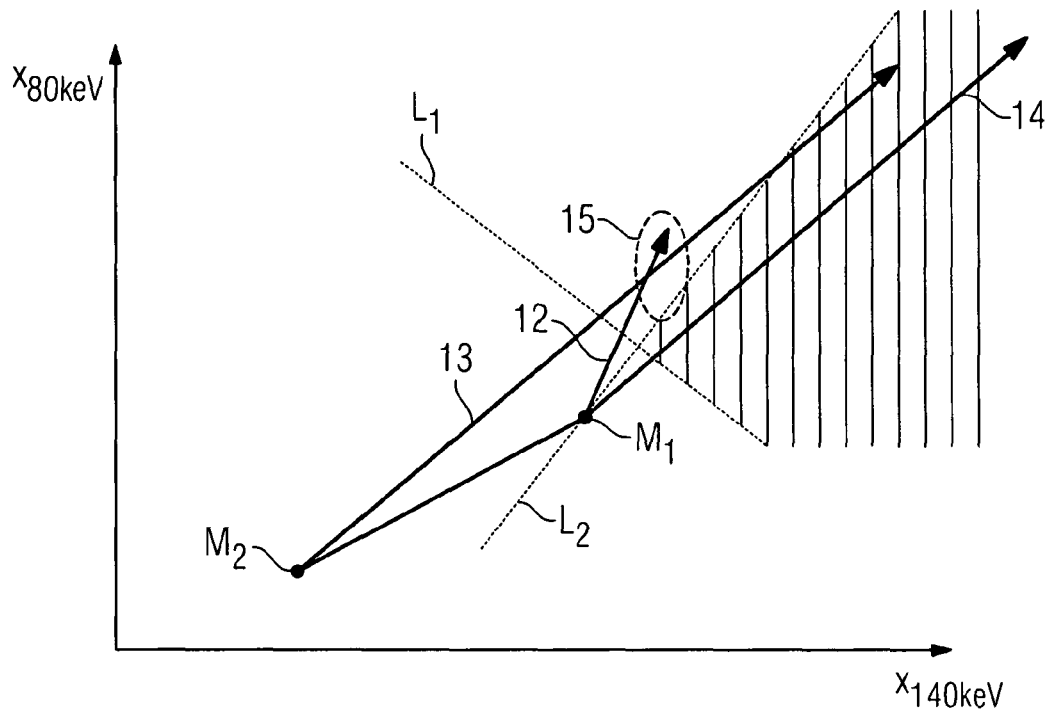
Figure 4:
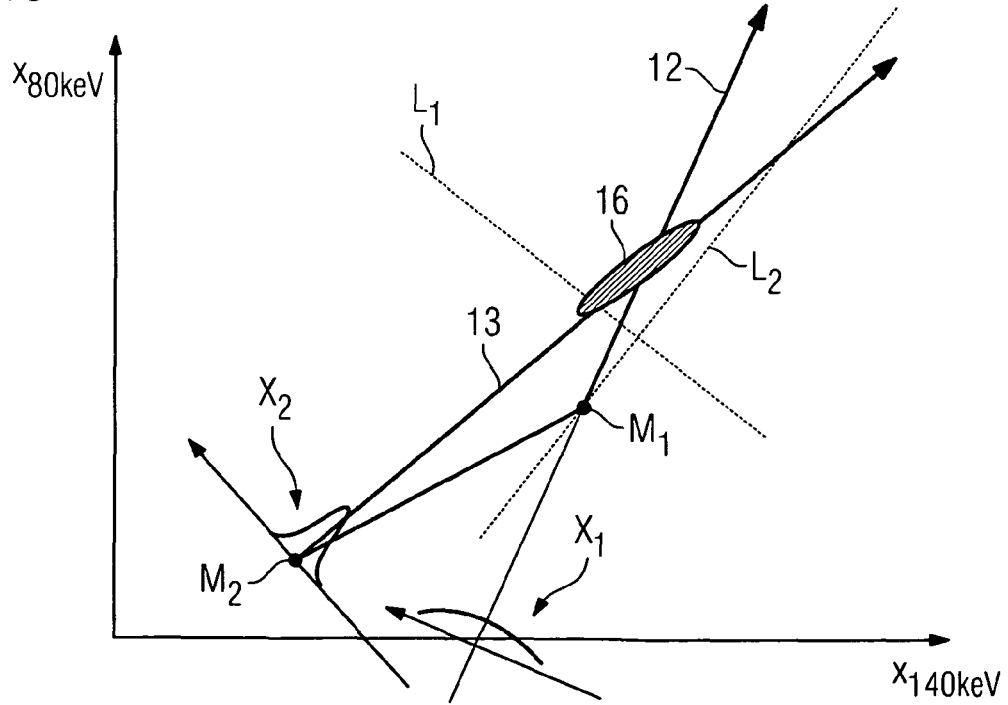

FIG. 1: shows an HU value diagram with HU values for four different materials;

FIG. 2: shows an HU value diagram illustrating an area associated with bone (for example according to the patent application with the file reference DE 10 2006 015 451.7, the entire contents of which are incorporated herein by reference);

FIG. 3: shows an HU value diagram in order to illustrate the association problem relating to fine vessels;

FIG. 4: shows an HU value diagram in order to illustrate the statistical analysis process carried out according to an embodiment of the invention; and FIG. 5: shows a dual-energy CT system for carrying out the method according to an embodiment of the invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The method according to an embodiment of the invention will be described using the following FIGS. 1 to 4 based on one preferred example of a CT contrast-agent examination with a dual-energy system. The aim in this case is to distinguish between the materials blood (=first material), contrast agent (=second material), predominantly dissolved in the blood, fat or yellow bone marrow (=third material) and bone (=fourth material), with two tomographic data records produced using different maximum X-ray energies of 80 keV and 140 keV being available for distinguishing purposes, which can already be associated with one another on the basis of pixels or voxels, because of the recording technique.

If these four materials are plotted on an HU value diagram showing the HU values of one material produced by a first energy spectrum on the ordinate and the HU values of this material produced by a second energy spectrum on the abscissa, then, by way of example, this results in a diagram as shown in FIG. 1 for the abovementioned materials and for X-ray radiation with respective maximum energies of 80 keV and 140 keV. The precisely determined values depend, of course, not only on the acceleration voltage, but also on the anode material used and on the pre-filtering of the X-ray radiation used. On the illustrated HU value diagram, the value pairs for $M_1$ correspond to blood, for $M_2$ for fat or yellow bone marrow, $M_3$ bone, and $M_4$ contrast agent containing iodine. The points $M_1$, $M_2$, $M_3$ and $M_4$ form an irregular quadrilateral in which the diagonals $M_1$-$M_4$ and $M_2$-$M_3$ are shown, and the gradients of the diagonals are calculated using:

$$m_{M1-M4} = \frac{x_{M4,80} - x_{M1,80}}{x_{M4,140} - x_{M1,140}} \text{ and } m_{M2-M3} = \frac{x_{M3,80} - x_{M2,80}}{x_{M3,140} - x_{M2,140}},$$

where $x_{y,z}$ are intended to denote the HU values of the material y when using the X-ray spectrum z.

A conventional dual-energy bone removal algorithm can be carried out as a first step, as described by way of example in the patent application with the file reference DE 10 2006 015 451.7, whose entire disclosure content is incorporated herein by reference. In this method, mean values are formed over the HU values at 80 keV and the HU value at 140 keV in the vicinity of the voxel to be analyzed. In this case, distinctions are drawn between mixtures composed of iodine and blood, as well as bone and soft tissue. Porous bone from the red bone marrow is also included, in similar amounts to blood in the soft tissue—correctly associated. Porous bone which contains yellow bone marrow is, however, identified as iodine in a certain range.

The reason for this is illustrated in FIG. 2. This figure once again shows the HU value diagram from FIG. 1, with the HU values for the materials fat $M_2$ and blood $M_1$. In addition, the arrows 11 and 12 denote the effect of enrichment by iodine, and the arrows 13 and 14 enrichment with bone substance. The shaded region which is defined by the two dashed separating lines $L_1$ and $L_2$ can be identified as bone. However, in some cases, yellow bone marrow in the spongiosa is located above the separating line L1 between iodine and bone in the area of the dashed ellipse 15. This means that, in reality, only voxels with relatively low HU values, which are identified as iodine by an algorithm based on mean values, may be mixtures of yellow bone marrow and bone.

Additional algorithm subsequent processing is therefore required for all voxels with this characteristic. According to an embodiment of the invention, the area around the voxel is statistically analyzed for this purpose. However, a hypothesis test is carried out, in contrast to a method based on threshold values. The distinction drawn in this case is which of the two possible material mixtures is the more probable.

An optimum method according to the invention is subdivided into six steps, in which case some steps are only optional:

1) A check is first of all carried out for each voxel to determine whether a relatively high HU value, that is to say a value above a predetermined threshold value, is measured sufficiently often (for example with a probability of 50%) in the surrounding area. This ensures that the subsequent evaluation is sufficiently statistically significant and that extended structures exist which are typical of bone marrow.

2) A highly smoothed image of the axial slice is considered, in which the voxel to be analyzed is present. The process is continued only if the smoothed image has a sufficiently high HU value at the position of the voxel. Specifically, this test excludes fine vessels which would otherwise lead to further ambiguities. This problem is illustrated schematically in FIG. 3. Specifically, if the central voxels in the vessel filled with iodine are located precisely on the connecting line between fat and bone, then partial volume effects with the surrounding tissue result in the mixture leading to voxels which are located exactly on the connecting line between yellow bone marrow and bone. This means that it is impossible to distinguish yellow bone marrow in the spongiosa.

The range of the image smoothing that has been mentioned should be matched to the apparent patient diameter since, for example, structures in the foot are typically finer than in the knee or in the abdomen.

3) A statistical analysis is carried out for those voxels in the area surrounding the voxel to be analyzed, with all the voxels under a specific threshold being excluded in order to avoid the statistics being dominated by mixtures with adjacent third materials (for example fat in addition to a blood/iodine mixture in a vessel).

By way of example, the threshold value is compared with the weighted HU value, which is calculated as follows from the HU value of the voxels at 80 keV and 140 keV:

The gradient $m_{co,min}$ is assumed to be between the gradient of the diagonals [blood, iodine] and the gradient of the diagonals [fat, bone]; q denotes the estimated ratio between the image noise at 80 keV and the image noise at 140 keV. The weighted HU value $x_m$ is then calculated as follows:

$$r = -\frac{q^2}{m_{co,min}} \text{ and } x_m = \frac{x_{80\text{ kV}} - r \cdot x_{140\text{ kV}}}{1-r}.$$

4) The following variants are calculated for all the selected voxels:

the signed distance $x_1$ of the voxel from the connecting line [blood, iodine],
the signed distance $x_2$ of the voxel from the connecting line [fat, bone].

The signed distance is calculated by means of a linear equation, for example:

$$x_1 = a_1 x_{80} + b_1 x_{140} + c_1$$

and $$x_2 = a_2 x_{80} + b_2 x_{140} + c_2.$$

5) The mean value $\langle x_1^2 \rangle$ and the mean value $\langle x_2^2 \rangle$ are now calculated. Furthermore, the mean value of $x_1$ and the variance of $x_1$ are calculated, with the latter always being less than or equal to the mean value $\langle x_1^2 \rangle$.

6) If the mean value of $x_1$ is greater than 0, that is to say the voxels are typically above the line [blood, iodine], then the following association is made:

Bone, if Var $x_1 > \langle x_2^2 \rangle$ otherwise:

Bone, if $\langle x_1^2 \rangle > \langle x_2^2 \rangle$.

This results in correct treatment even of large-area mixtures of fat and soft tissue, for example in the liver.

The decision can also be modified by factors so that, for example, only what is very certainly bone is removed.

In addition, a correction can be applied when the noise ratio q can assume very extreme values and the connecting lines [iodine, blood] and [fat, bone] are assumed to have very different gradients:

$$\langle x_1^2 \rangle \to \frac{\langle x_1^2 \rangle}{a_1^2 q^2 + b_1^2},$$

$$\langle x_2^2 \rangle \to \frac{\langle x_2^2 \rangle}{a_2^2 q^2 + b_2^2},$$

$$\mathrm{Var}(x_1^2) \to \frac{\mathrm{Var}(x_1^2)}{a_1^2 q^2 + b_1^2}.$$

The operation of the algorithm is illustrated schematically in FIG. 4. The distribution of the voxels is shown as a shaded ellipse. As can clearly be seen in the illustration, the distribution of the voxels on the $x_1$ coordinate after projection is very much broader than on the coordinate $x_2$, that is to say this is identified as bone.

In principle, the proposed method can also be used to distinguish between more than two mixtures of two materials each. This is done by testing not only two alternatives but by calculating different $x_i$ based on the hypotheses. That hypothesis i with the minimum value $\langle x_i^2 \rangle$ is finally selected.

In general, the method can be used whenever it is necessary to distinguish between mixtures each composed of two materials, but with the mixtures being sufficiently inhomogeneous so that sufficiently different mixture ratios may occur in the area surrounding a voxel to be classified.

The advantages of the method include the fact that the algorithm is highly tolerant to noise. In addition, there is no need to define segmentation areas in the two-dimensional feature space. Furthermore, no absolute segmentation is carried out, with just two possible hypotheses being compared. This avoids the need to search for suitable threshold values.

This method as described above and a method which has been modified in accordance with the idea on which the invention is based can preferably be carried out in a control and computation unit of a CT system or else in a separate computation unit. FIG. 5 illustrates an example of a CT system 1 such as this. This CT system 1 has a gantry housing 6 in which two X-ray tubes 2 and 4 with opposite detector systems 3 and 5 are arranged at offset angles and rotate around a system axis 9 in order to scan the patient 7, while the patient 7 is moved by means of the controllable patient couch along the system axis 9 through the measurement area of the CT system. In the example illustrated here, the two X-ray tubes 2 and 4 are operated with different acceleration voltages, so that the two X-ray spectra that are used differ widely and also result in different absorption values in the associated detectors as the radiation passes through the patient.

A control and computation unit 10 whose memory contains computer programs $Prg_1$-$Prg_n$ which carry out the control and reconstruction processes during operation is used to control, reconstruct and carry out the method according to the invention. These programs also include at least one program $Prg_x$ which carries out a method according to an embodiment of the invention.

As a precaution, it should be noted that the described method can be carried out not only with the CT system illustrated here with two X-ray tubes that are operated at the same time. It is also possible to gather records with different energy spectra using a CT system with a single tube/detector system so that—if required after previous registration of the records—the method described above can be carried out. An energy-resolving detector can also be used as one variant.

It is self-evident that the features of embodiments of the invention mentioned above can be used not only in the respectively stated combination but also in other combinations or on their own without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for distinguishing between four materials ($M_1$, $M_2$, $M_3$, $M_4$) in tomographic records of a dual-energy Computed Tomography (CT) system, the method comprising:

scanning of an examination area of an examination object, including at least four different materials ($M_1$, $M_2$, $M_3$, $M_4$), wherein the scanning is carried out using two different X-ray energy spectra from a multiplicity of projection directions, and absorption data is measured for each X-ray spectrum that is used, Hounsfield Units (HU) values of four materials ($M_1$, $M_2$, $M_3$, $M_4$) form a quadrilateral on an HU-value diagram of the X-ray spectra used for scanning, the two diagonals ($M_1$-$M_4$, $M_2$-$M_3$) of which quadrilateral intersect one another, the materials which form one diagonal are each mixed, and two materials which define a diagonal form a mixture with particle sizes in the same order of magnitude as the resolution of the CT system;

reconstructing at least one first tomographic image data record from the absorption data of the first X-ray spectrum;

reconstructing at least one second tomographic image data record from the absorption data of the second X-ray spectrum;

defining a size of at least one of a two-dimensional and three-dimensional viewing area around each voxel whose material content is to be distinguished, and carrying out subsequent statistical calculations in the viewing area;

imaging adjacent voxels from the viewing area on an HU value diagram, for each voxel whose material content is to be distinguished;

calculating distances ($x_1$, $x_2$) from the diagonals ($M_1$-$M_4$, $M_2$-$M_3$) for all the imaged voxels, and forming a mean squares of the distances ($\langle x_1^2 \rangle$, $\langle x_2^2 \rangle$); and assuming, when the mean square distance ($\langle x_1^2 \rangle$, $\langle x_2^2 \rangle$) to one diagonal is less than to the other diagonal, that the composition of the voxel is composed of the materials ($M_1+M_4$, $M_2+M_3$) to whose diagonal the lower mean square distance ($\langle x_1^2 \rangle$, $\langle x_2^2 \rangle$) occurs.

2. The method as claimed in claim 1, wherein the method is carried out only for those voxels whose adjacent voxels in the viewing area, at least in one of the image data records at least one of overshoot and undershoot a HU threshold value for a proportion.

3. The method as claimed in claim 2, wherein, in order to carry out the method, at least one of the image data records is smoothed in advance in at least one direction and is continued only when the smoothed image overshoots a threshold at this point.

4. The method as claimed in claim 3, wherein the smoothing is carried out two-dimensionally on one plane.

5. The method as claimed in claim 4, wherein the smoothing is carried out on the axial slice image plane.

6. The method as claimed in claim 3, wherein the smoothing is carried out on the axial slice image plane.

7. The method as claimed in claim 3, wherein the smoothing is carried out three-dimensionally in space.

8. The method as claimed in claim 1, wherein the statistical analyses include only those voxels whose HU values overshoot a threshold value in at least one image data record.

9. The method as claimed in claim 8, wherein a specific threshold value is used for each image data record.

10. The method as claimed in claim 1, wherein the only voxels which are included in the statistical analyses are those whose HU value ($x_m$), weighted as a function of the noise, from the two image data records overshoots a threshold value.

11. The method as claimed in claim 10, wherein, for the HU value, weighted as a function of the noise, of each voxel, $$r = -\frac{q^2}{m_{co,min}} \text{ and } x_m = \frac{x_{E1} - r \cdot x_{E2}}{1 - r},$$

where:

q corresponds to the ratio ($q_{E1}/q_{E2}$) between the noise ($q_{E1}$) of the image data record ($B_{E1}$) with the first X-ray energy ($E_1$) to the noise ($q_{E2}$) of the image ($B_{E2}$) with the second X-ray energy ($E_2$), and $m_{co,min}$ corresponds to a value which is between the gradients of the diagonals on the HU value diagram of the four materials.

12. The method as claimed in claim 1, wherein blood is regarded as the first material ($M_1$), fat as the second material ($M_2$), bone as the third material ($M_3$), and a contrast agent as the fourth material ($M_4$).

13. The method as claimed in claim 12, wherein a contrast agent containing iodine is used as the contrast agent.

14. The method as claimed in claim 12, wherein a contrast agent containing lanthanoid is used as the contrast agent.

15. The method as claimed in claim 1, wherein blood is regarded as the first material ($M_1$), air as the second material ($M_2$), bone as the third material ($M_3$), and a contrast agent as the fourth material ($M_4$).

16. The method as claimed in claim 15, wherein a contrast agent containing iodine is used as the contrast agent.

17. The method as claimed in claim 15, wherein a contrast agent containing lanthanoid is used as the contrast agent.

18. The method as claimed in claim 1, wherein:

the signed mean distances ($\langle x_1 \rangle$, $\langle x_2 \rangle$) to the two diagonals and the variance ($\text{Var}(x_1)$) of the distances to the diagonals between the first and the fourth material are calculated with respect to the HU value diagram in addition to the mean squares of the distances ($\langle x_1^2 \rangle$, $\langle x_2^2 \rangle$), and when the signed mean distance ($<x_1>$) to the first diagonal between the first and the fourth material is positive ($\langle x_1 \rangle > 0$) and the variance of this mean distance of the voxels ($V_{ij}$) which are located in the viewed area is greater than the mean square distance ($\text{Var}(x_1) > \langle x_2^2 \rangle$), or when the mean square distance from the first diagonal is greater than the mean square distance from the second diagonal between the second material and the third material ($\langle x_1^2 \rangle > \langle x_2^2 \rangle$) it is assumed that the voxel under consideration is composed of the second and third materials.

19. The method as claimed in claim 1, wherein the mean square distances ($\langle x_1^2 \rangle$, $\langle x_2^2 \rangle$) are replaced using the following formulae:

$$\langle x_1^2 \rangle \rightarrow \frac{\langle x_1^2 \rangle}{a_1^2 q^2 + b_1^2},$$

$$\langle x_2^2 \rangle \rightarrow \frac{\langle x_2^2 \rangle}{a_2^2 q^2 + b_2^2}$$

where q corresponds to the ratio ($q_{E1}/q_{E2}$) between the noise ($q_{E1}$) of the image data record ($B_{E1}$) with the first X-ray energy ($E_1$) to the noise ($q_{E2}$) of the image ($B_{E2}$) with the second X-ray energy ($E_2$), and the coefficients $a_1$, $a_2$, $b_1$ and $b_2$ are calculated as follows:

$$a_1 = \frac{1}{\sqrt{1 + m_{M2-M3}^2}},$$

$$a_2 = \frac{1}{\sqrt{1 + m_{M1-M4}^2}},$$

$$b_1 = -\frac{m_{M2-M3}}{\sqrt{1 + m_{M2-M3}^2}}$$

$$b_2 = -\frac{m_{M1-M4}}{\sqrt{1 + m_{M1-M4}^2}}.$$

20. A CT system having
a gantry housing which rotates at least one x-ray tube with opposite detector system around a system axis to scan a patient;
a controllable patient couch movable along the system axis; and
a computation unit containing
a memory with program code for carrying out the method steps as claimed in claim 1, and
a processor configured to execute the program code contained in the memory to implement the method of claim 1.

21. A non-transitory computer readable medium including program segments for, when executed on a computer device, causing the computer device to implement the method of claim 1.

* * * * *